United States Patent [19]
Jack et al.

[11] Patent Number: 5,719,396
[45] Date of Patent: Feb. 17, 1998

[54] SYSTEMS AND METHODS FOR DETERMINING COMPLIANCE OF MOVING VEHICLES WITH EMISSION-CONCENTRATION STANDARDS

[75] Inventors: Michael D. Jack, Goleta; Troy P. Bahan, Santa Barbara; Jeffrey L. Hanson, Lompoc; David R. Nelson, Santa Barbara; Allen J. Paneral; Jay Peterson, both of Goleta, all of Calif.

[73] Assignee: Envirotest Systems Corp., Sunnyvale, Calif.

[21] Appl. No.: 674,075

[22] Filed: Jul. 1, 1996

[51] Int. Cl.$^6$ .................................................. G01N 21/00
[52] U.S. Cl. .............................. 250/338.5; 250/339.13; 250/373
[58] Field of Search .......................... 250/338.5, 339.13, 250/373

[56] References Cited

U.S. PATENT DOCUMENTS

| | | | |
|---|---|---|---|
| 4,924,095 | 5/1990 | Swanson, Jr. | 250/338.5 |
| 5,343,043 | 8/1994 | Johnson | 250/338.5 |
| 5,418,366 | 5/1995 | Rubin et al. | 250/338.5 |
| 5,489,777 | 2/1996 | Stedman et al. | 250/338.5 |
| 5,498,872 | 3/1996 | Stedman et al. | 250/338.5 |

OTHER PUBLICATIONS

US Patent Application Serial No. 08/318,566 in the name of Jack, Michael D., et al., filed Oct. 5, 1994 for "Optical Sensing Apparatus for Remotely Measuring Exhaust Gas Composition of Moving Motor Vehicles".

*Primary Examiner*—Michael J. Tokar
*Assistant Examiner*—Virgil O. Tyler
*Attorney, Agent, or Firm*—Hunton & Williams

[57] ABSTRACT

An emission-concentration monitoring system (20) includes first and second monitor stations (22,32) which are separated by a sensing space (40) along a path (28) of a moving vehicle (26). Each station has a source of electromagnetic radiation (64) which is directed through the vehicle's exhaust plume. Each station also has a set of detectors (66) which are positioned to receive the radiation and configured to measure transmittances at wavelengths which are absorbed by molecular species of exhaust plume (e.g., hydrocarbons, nitric oxide, carbon monoxide and carbon dioxide). These sensed transmittances are converted to emission concentrations by a data processor (50) and compared to a set of emission-concentration standards. The vehicle is determined to be in violation only if its emission concentrations at both the first and second monitor stations exceeds the standards. To insure visual identification of the vehicle, images of it are formed at both stations with video cameras (42, 44) and a license plate reader (46). It has been found that the monitoring system improves testing accuracy because the first and second stations essentially form a check against each other to remove errors due, for example, to vehicular temporal variabilities.

32 Claims, 6 Drawing Sheets

SYSTEMS AND METHODS FOR DETERMINING COMPLIANCE OF MOVING VEHICLES WITH EMISSION-CONCENTRATION STANDARDS

BACKGROUND THE INVENTION

1. Field of the Invention

The present invention relates generally to vehicular emission sensing.

2. Description of the Related Art

Federally-mandated emission standards have been set for emission concentrations from motor vehicle tailpipes. These standards set maximum concentrations (generally expressed as percentages) of the total gas volume from tailpipes for various molecular species, e.g., hydrocarbons (HC), nitric oxide (NO), carbon monoxide (CO) and carbon dioxide ($CO_2$). The compliance of motor vehicles to these standards is typically measured in mandatory periodic inspections which are performed at fixed facilities in accordance with officially-approved test procedures.

For example, emission tests in accordance with Federal Test Procedures (FTP) ("Instrumentation and Techniques for Exhaust Gas Emission Measurements", Society of Automotive Engineers, documents J254 and J1094, August 1994) require that a vehicle be placed on a dynamometer and exercised over various operating modes (e.g., acceleration, cruising and deceleration) for ~1 hour while the tailpipe concentrations are measured.

Tests in accordance with Inspection-Maintenance Procedure 240 (IM240) ("High Tech I/M Test Procedure, Emission Standards, Quality Control Requirements and Equipment Specification—Final Technical Guidance", United States Environmental Protection Agency, Report EPA-AA-EPSD-LM-93-1, April 1994 AIR) are conducted in a similar manner but with the time period reduced to ~240 seconds.

After passing these periodic inspections, however, some owners remove or disable the emission control devices of their vehicles because they perceive that these devices degrade vehicle performance. Other owners simply ignore notices of the mandatory periodic inspections. Accordingly, many regulatory agencies have supplemented the periodic fixed-facility tests with unannounced tests that are intended to measure emission concentrations of moving vehicles with portable measurement equipment that is temporarily set up at remote sites, e.g., streets and highways.

These roadside tests must sense emission concentrations from rapidly moving vehicles with portable equipment. In addition, they must be conducted without direct access to the vehicle tailpipe. Accordingly, it has been difficult to obtain satisfactory correspondence between emission concentrations measured in these tests and those measured for the same vehicles when retested at fixed facilities in accordance with the FTP or IM240 test procedures.

Moving vehicle tests typically utilize the fact that each molecular species of interest in an exhaust plume absorbs radiation at a specific wavelength. For example, HC, NO, CO and $CO_2$ absorb different wavelength radiations in the 3–6 µm region of infrared radiation. Thus, transmittances at these wavelengths of an infrared beam which has passed through an exhaust plume is indicative of the concentration of these molecular species in the plume. Nonetheless, the concentration of NO is particularly difficult to accurately measure because of significant interference from water absorption in bands which are adjacent the 5.2 µm radiation region that NO absorbs. However, apparatus and methods for measuring NO concentration in an exhaust plume have now been developed.

For example, a system for detecting NO in vehicular exhaust plumes was described in U.S. Pat. No. 5,418,366 to Rubin, Lane H., et al. which issued May 23, 1995 and was assigned to Santa Barbara Research Center, the assignee of the present invention. In the teachings of this Patent, transmittance of an infrared beam is sensed at four wavelengths with respective photodetectors to determine a) NO transmittance at a first wavelength of 5.26 µm, b) water ($H_2O$) transmittance at a second wavelength of 5.02 µm, c) $CO_2$ transmittance at a third wavelength of 4.21 µm and d) a reference transmittance at a fourth wavelength of 3.8 µm that is not significantly absorbed.

The reference transmittance is used to compensate the other transmittances for radiation variations caused by a) fluctuations in the output of the radiation source that generates the infrared beam, b) particulate matter in the form of road dust and c) particulate matter in the exhaust plume. Thus, the reference transmittance acts to form a baseline output which is independent of the molecular species in the exhaust plume.

A lookup table is provided which contains correction factors that relate $H_2O$ absorption at the 5.02 µm wavelength to that at the 5.26 µm wavelength. Preferably, a calibration cell is also provided which contains a heated mixture of gases (e.g., NO, $CO_2$ and $H_2O$) in predetermined gas concentrations and the cell is configured so that the path length through the mixture can be selected. The calibration cell can be selectively inserted in the infrared beam to calibrate the NO, $CO_2$ and $H_2O$ photodetectors with respect to each other.

In operation of this system, a data processor first uses a correction factor from the lookup table to convert the sensed $H_2O$ transmittance to one at 5.26 µm wavelength. This converted $H_2O$ transmittance and the reference transmittance are used to compensate the sensed NO transmittance and derive an effective NO transmittance. This effective NO transmittance can then be processed along with the sensed transmittances of other molecular species to determine tailpipe emission concentrations.

This processing is exemplified in copending U.S. patent application Ser. No. 08/318,566 which was filed Oct. 10, 1994 in the name of Jack, Michael D., et al. and was assigned to Santa Barbara Research Center, the assignee of the present invention. This application is directed to an optical sensing apparatus for remotely measuring the exhaust gas composition of moving motor vehicles.

In this apparatus, an infrared beam (from an infrared source, e.g., a glow bar, whose radiation wavelengths include the 3–6 µm region) is positioned to pass through the exhaust plume of a moving vehicle before being received by a photodetector assembly. This assembly includes an optical beam integrator which has optical structure (e.g., a plurality of refractive lens facets which superimpose different segments of the beam) that reduces spatial and temporal variations in the infrared beam. The beam then passes through a plurality of optical filters and is incident upon a plurality of closely spaced photodetectors (e.g., mercury cadmium telluride photoconductive detectors).

Each optical filter (formed, for example, from multiple layers of a dielectric such as zinc sulfide) passes a band of infrared radiation that is centered about a predetermined wavelength to its respective photodetector. These predetermined wavelengths are selected to sense the infrared absorption that is caused by the presence of different molecular species in the exhaust plume. The wavelengths and their respective molecular species include 5.26 μm-NO, 5.02 μm-H$_2$O, 4.6 μm-CO, 4.2 μM-CO$_2$ and 3.3 μm-HC. In addition, a reference transmittance is measured at a nonabsorbing wavelength of 3.8 μm.

Because the exhaust plume is itself an infrared radiation source, the output of the photodetectors is formed of a first portion that corresponds to the infrared source and a second portion that corresponds to the exhaust plume. A radiation chopper is positioned to alternately pass and block the radiation of the infrared source so that the apparatus can sense and subtract the second portion.

The concentrations of these molecular species progressively decay after their emission from a vehicle tailpipe. In addition, it is difficult to determine the path length of the infrared beam through the exhaust plume. Thus, the transmittances which are sensed by the photodetector assembly represent products of concentrations and pathlengths that vary with time and which are indeterminate. Accordingly, the transmittances cannot be compared directly with tailpipe concentration standards.

However, it is known that these molecular species disperse at the same rate. Therefore, the measured transmittance ratios of NO/CO$_2$, CO/CO$_2$ and HC/CO$_2$ will be substantially constant. In addition, known chemical relationships of the combustion process teach that the CO$_2$ concentration is a function of the carbon/hydrogen ratio of the vehicle's fuel. This latter ratio and the measured transmittance ratios form the basis for calculation of the CO$_2$ concentration. Finally, the measured transmittance ratios are multiplied by the determined CO$_2$ concentration to yield the desired concentrations of HC, NO and CO.

Prior to this measurement process, the NO transmittance is first converted to an effective transmittance as described above with reference to U.S. Pat. No. 4,916,361.

In operation of this detecting apparatus, the sensed transmittances are digitized in an analog-to-digital converter and processed as described above in a data processor. A trigger signal is generated when a sharp drop and a subsequent rise in the measured transmittances indicate that a moving vehicle has interrupted the infrared beam. In response to this trigger signal, the apparatus stores measurements prior to the trigger as a measure of clean air preceding the vehicle and measurements after the trigger as a measure of the exhaust plume. In addition, a video camera is positioned to capture a video image of the vehicle's license plate.

The apparatus can be set to the following operational modes: a) storage of emission and video data on all monitored vehicles for database purposes (e.g., comparison of exhaust concentrations and vehicle types) and b) storage of emission and video data only for vehicles which exceed emission standards. Data from the latter mode can be retrieved at a later time for law enforcement use, e.g., to send emission violation notices to vehicle owners.

The HC, NO, CO and CO$_2$ concentrations are displayed on a monitor along with the license plate image and the combined concentration and video data is also stored in a suitable storage device, e.g., a video recorder. Preferably, the display shows measured concentrations of CO, CO$_2$ and HC as a function of time, the slopes, intercepts and standard deviations of the measured NO/CO$_2$, CO/CO$_2$ and HC/CO$_2$ transmittance ratios and the peak-to-peak outputs of the photodetectors.

The measurement time through the exhaust plume of a moving vehicle is typically on the order of one second. It has been found that the emission concentrations measured by this apparatus substantially agree with fixed-facility measurements during corresponding time intervals. However, vehicle emissions vary with parameters that include vehicle operating mode (e.g., acceleration, cruise and deceleration), throttle position and individual driver behavior. In addition, marginal vehicles often have high emission concentrations momentarily. Thus, they will meet emission standards at one moment and fail at another.

The fixed-facility tests integrate these measurements over a relatively long time interval so that most of these temporal variabilities are ignored. Because this is not possible in moving vehicle tests, their test results disagree with those of the fixed facilities at a disagreement rate high enough to degrade the attractiveness of presently available portable test apparatus to law-enforcement and regulatory agencies.

SUMMARY OF THE INVENTION

The present invention is directed to systems and methods for determining compliance of moving vehicles with emission-concentration standards. In particular, to systems and methods which obtain substantial agreement with fixed-facility emission tests run in accordance with approved test procedures (e.g., IM240 and FTP test procedures).

These goals are achieved with a monitoring system that includes first and second monitoring stations which are spaced apart by a sensing space along the path of a moving vehicle. Each monitoring station includes a source of electromagnetic radiation that directs an electromagnetic beam through an exhaust plume of a moving vehicle and a set of electromagnetic detectors which receive the beam and detect a plurality of beam transmittances.

These transmittances are sensed at a plurality of selected wavelengths at which different molecular species absorb the beam's radiation. A data processor converts the transmittances into emission concentrations which are compared to a set of predetermined emission-concentration standards. The vehicle is determined to be in violation only if the emission concentrations measured at both of the first and second monitor stations exceed the standards. In another compliance-mode of operation, the vehicle is determined to be in violation if an average of the emission concentrations at the first and second monitor stations exceeds the standards.

Systems of the invention improve testing accuracy because the spaced first and second stations essentially form a check against each other to remove temporal test errors. In particular, tests of an exemplary infrared prototype have indicated that separating the two monitoring stations by a sensing space effectively reduces test disagreements with subsequent IM240 emission-concentration tests as compared to single-station prototypes (e.g., from 40–50% to <10%).

In seeking a balance between a large sensing space that reduces system congestion and a small sensing space that reduces cable lengths, it has been determined that the sensing space is preferably set between 15 and 45 meters.

The monitoring system also includes imaging devices which are positioned to form images of moving vehicles at the first and second monitor stations. These images verify that the same vehicle was the source of the emission concentrations that exceeded the standards.

To reduce data in a compliance mode of operation, the system is configured to store only emission-concentration data from vehicles that are determined to be in violation. The system can be placed in an alternate data-gathering mode in which data is stored from all monitored vehicles.

The novel features of the invention are set forth with particularity in the appended claims. The invention will be best understood from the following description when read in conjunction with the accompanying drawings.

DETAILED DESCRIPTION OF THE PREFERRED EMBODIMENTS

Figure 1:
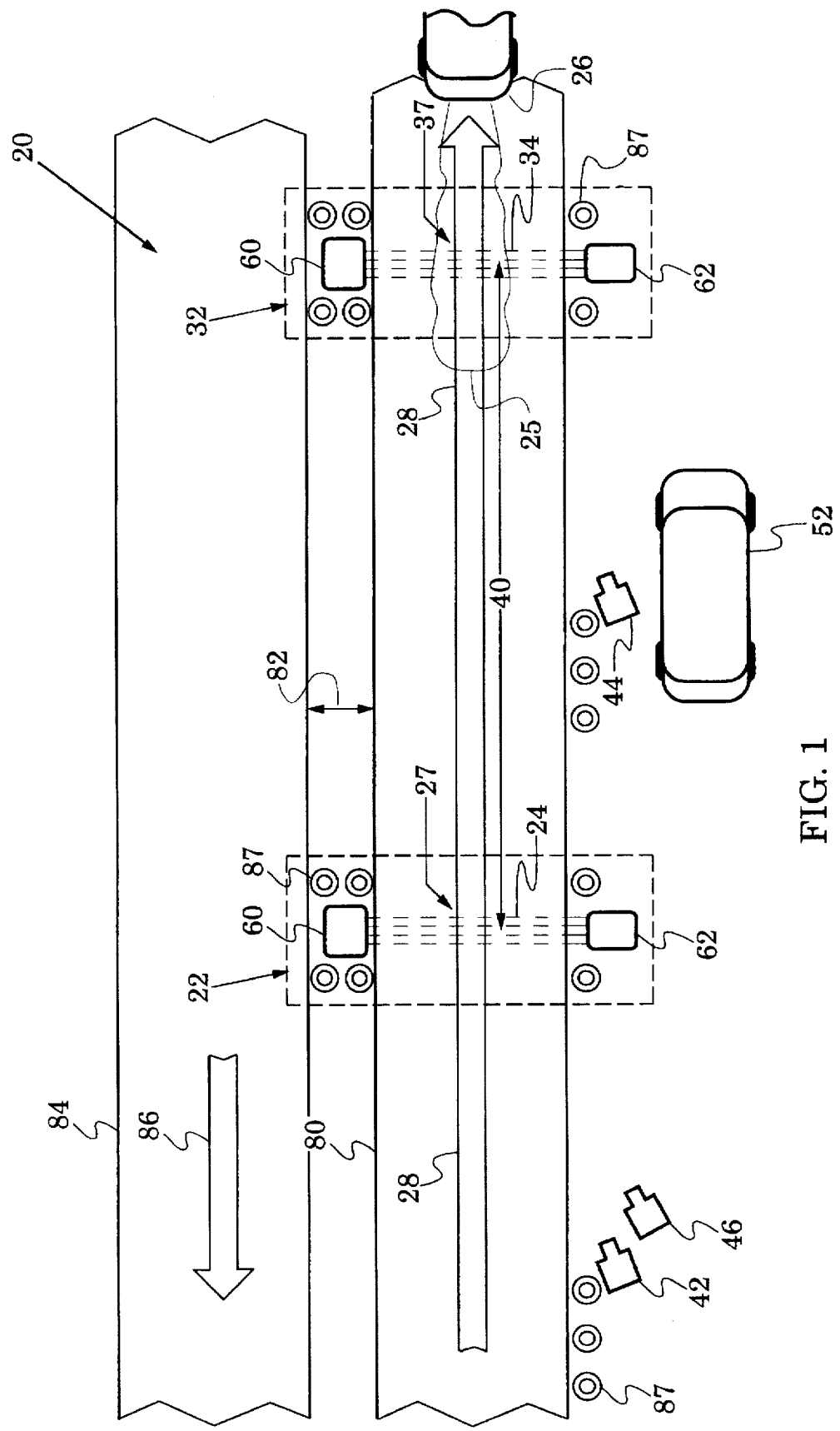
FIG. 1 is a plan view of an emission-concentration monitoring system in accordance with the present invention.
Figure 2:
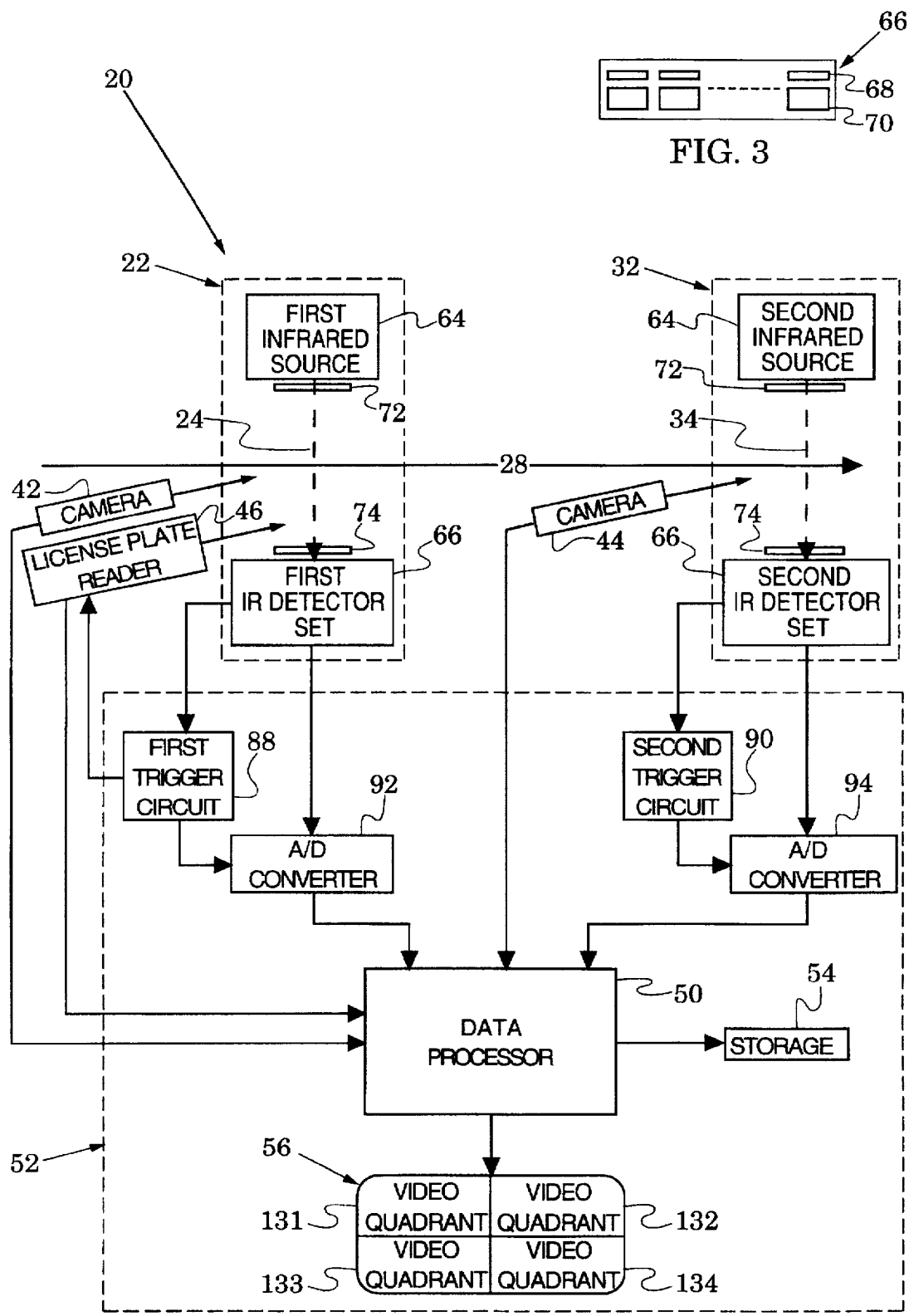
FIG. 2 is a block diagram of the monitoring system of FIG. 1.

FIGS. 1 and 2 illustrate an emission-concentration monitoring system 20 which is especially suited for determining compliance of moving vehicles with emission-concentration standards. The system 20 includes a first monitor station 22 which is configured and positioned to direct a first beam 24 of electromagnetic radiation through the exhaust plume of a moving vehicle (e.g., the plume 25 and vehicle 26 of FIG. 2) at a first location 27 along a path 28 of the vehicle (the vehicle's direction is indicated by the path arrow 28).

The system 20 also includes a second monitor station 32 which is positioned to direct a second beam 34 of electromagnetic radiation through the exhaust plume at a second location 37 along the path 28 which is spaced from the first location 26 by a sensing space 40. Each monitor station is also configured to detect beam transmittances through the plume (received power through plume/received power in absence of plume) at a plurality of selected wavelengths.

Video cameras 42 and 44 are positioned to form images of the rear of the vehicle at the first and second locations 27 and 37 respectively. In addition, a license plate reader 46 (a video camera equipped with a character reading and digitizing processor) is positioned to generate a digital signal representative of the license plate number of the moving vehicle.

As especially shown in FIG. 2, the collective data from the first and second monitor stations 22 and 32, the video cameras 42 and 44 and the license plate reader 46 is coupled to a data processor 50 which is housed in a van 52 (indicated by broken lines in FIG. 2) that is preferably positioned between the monitor stations to enhance the system's compactness, reduce costs and reduce signal paths (e.g., the cable paths between stations and van). Storage devices 54 (e.g., video cassette and hard disk) and a video monitor 56 are coupled to receive data from the data processor 50.

In the basic operation of the monitoring system 20, a first set of emission concentrations (e.g., concentrations of NO, HC, CO and $CO_2$) are determined based upon interrogation of an exhaust plume of a vehicle by the first monitor station 22. Similar emission concentrations are determined based upon interrogation of the exhaust plume by the second monitor station 32. These determined emission concentrations are compared to emission-concentration standards and the vehicle is determined to fail compliance with the emission standards only if the first and second sets of emission concentrations both exceed the emission-concentration standards.

In tests of an exemplary infrared prototype of the emission-concentration monitoring system 20, its compliance decisions were compared with those of subsequent IM240 emission-concentration tests. It was found that the disagreement rate was significantly reduced, e.g., from 40–50% to <10%, compared to disagreement rates of single-station prototypes. It is theorized that the high disagreement rate of single-station prototypes is caused by the temporal variability of vehicular emissions and that the spatial separation of the first and second monitor stations 22 and 32 in the monitoring system 20 improves measurement accuracy because the stations essentially form a check against each other to remove temporal errors.

It has been found that disagreement rates are improved as soon as the sensing space 40 is made sufficient to accommodate the equipment of the monitor stations, e.g., >1 meter (for average vehicle speed, this translates into a sensing time interval that is greater than ~70 milliseconds). In seeking a balance between a large sensing space that reduces system congestion and a small sensing space that reduces cable lengths, it has been determined that a sensing space between 15 and 45 meters (time interval of ~1–3 seconds) is an effective compromise.

As shown in FIG. 1, each of the monitor stations 22 and 32 has an electromagnetic source 60 and an electromagnetic receiver 62 which are positioned on opposite sides of the vehicle path 26. Each receiver 62 is configured to detect wavelength-selective absorption of its respective electromagnetic beam by different molecular species in the plume 25.

Figure 3:
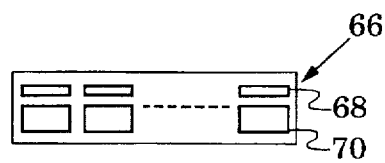
FIG. 3 is a block diagram of a set of infrared detectors in the monitoring system of FIG. 1.

In an infrared embodiment shown in FIGS. 2 and 3, the source is an infrared source 64, e.g., a glow bar, whose radiation has wavelengths spanning the 3–6 μm infrared region and the receiver includes a set 66 of infrared detectors. As shown in FIG. 3, each set 66 has a plurality of optical bandpass filters 68 which are configured to each pass a respective one of the selected wavelengths and a plurality of photodetectors 70 (e.g., mercury cadmium telluride photoconductive detectors) which are each positioned to receive filtered infrared radiation from a respective one of the filters.

Preferably, each of the monitor stations 22 and 28 also includes a chopper 72 which periodically interrupts the infrared beams (interrupted beams are indicated in FIGS. 1 and 2) prior to their travel through vehicle exhaust plumes so that the system 20 can sense and subtract infrared radiation emitted by the exhaust plume. The stations also preferably have a beam integrator 74 which reduces spatial and temporal variations of the infrared beams 24 and 34 before they are incident upon the detector sets 68.

FIG. 1 illustrates that the van 52, the video cameras 42 and 44, the license plate reader 46 and the receivers 62 of each monitor station are preferably positioned along an outer side of a vehicle lane 80. The sources 60 of each monitor station are preferably positioned on the inner side (e.g., in a median strip 82 between the vehicle lane 80 and another vehicle lane 84 along which vehicles pass in an oppositely-directed path 86). As a safety precaution, traffic cones 87 are distributed about the system 20.

An exemplary operation of the monitoring system 20 begins when the vehicle 26 passes through the infrared beams 24 and 34. In response, the transmittances sensed by the detector sets 66 at the first and second monitor stations 22 and 32 momentarily drop and rise. In response to the rising edge of these signals, first and second trigger circuits 88 and 90 send trigger signals respectively to analog-to-digital converters 92 and 94. In response to these trigger signals, the converters 92 and 94 pass transmittance data from the receivers of the first and second monitor stations 22 and 32 to the data processor 50 and visual-identification data is coupled to the data processor from the imaging devices 42, 44 and 46.

Figure 4:
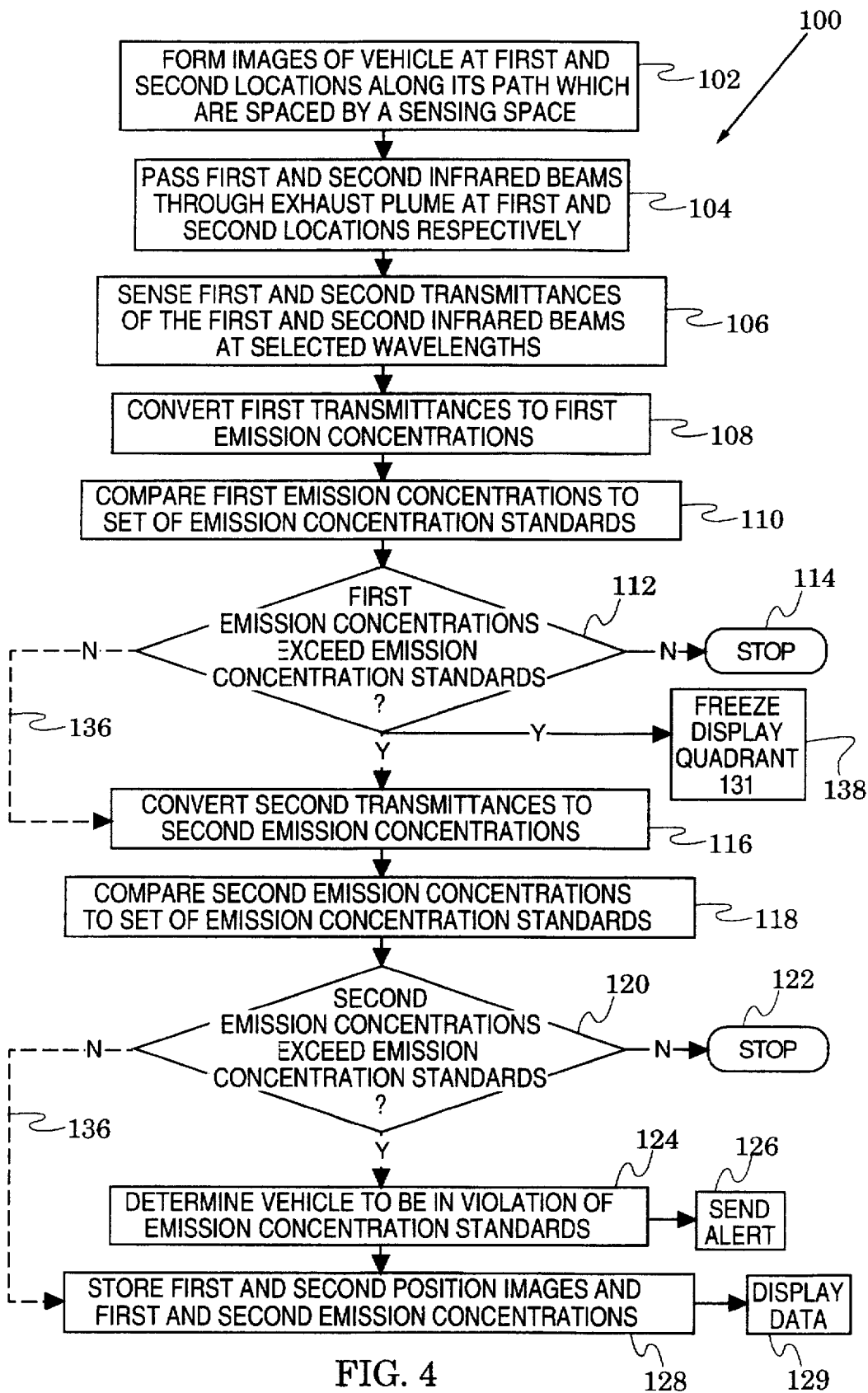
FIG. 4 is a flow diagram which illustrates compliance and data-gathering operational modes of the monitoring system of FIG. 1.

In a compliance-mode operation of an infrared embodiment of the monitoring system 20, data processor 50 is programmed in accordance with the flow diagram 100 of FIG. 4. In process step 102, images of a vehicle are formed at first and second vehicle locations (27 and 37 in FIGS. 1 and 2) which are spaced along the vehicle's path by a sensing space (40 in FIGS. 1 and 2). These images are formed by the video cameras and license plate reader (42, 44 and 46 in FIGS. 1 and 2) and coupled to the data processor (50 in FIGS. 1 and 2).

In process step 104, first and second infrared beams are passed through the exhaust plume of the vehicle respectively at the first and second vehicle locations. In process step 106, first and second transmittances (respectively of the first and second beams) are sensed at a plurality of selected wavelengths (e.g., at wavelengths that are absorbed by emissions of NO, HC, CO and $CO_2$). This sensing is performed by the detector sets 66 of FIG. 2.

The first transmittances are converted to first emission concentrations in process step 108 and compared to a set of emission-concentration standards in process step 110. At decision step 112, the process stops at terminator 114 if the first emission concentrations do not exceed the emission-concentration standards and proceeds to process step 116 if they do exceed the standards.

The second transmittances are converted to second emission concentrations in process step 116 and compared to the set of emission-concentration standards in process step 118. At decision step 120, the process stops at terminator 122 if the second emission concentrations do not exceed the emission-concentration standards and proceeds to process step 124 if they do exceed the standards.

In process step 124, the vehicle is determined to be in violation of the emission-concentration standards and, in process step 126, an alert is sent to a law-enforcement agency which may choose to pull over the violating vehicle for citing. Finally, in process step 128 the first and second images and the first and second emission concentrations are stored in storage media (54 in FIG. 2). This data can also be provided along with the alert to the law-enforcement agency.

In this compliance mode of operation, data is stored only when the first and second emission concentrations exceed the emission-concentration standards. This data storage feature greatly reduces the amount of stored data and also reduces the workload of a system operator in the van 52 because the operator's attention is not distracted by nonviolating vehicle data.

As indicated by process step 129, the data is also sent to the video monitor 56 of FIG. 2 for display in the van 52. In an exemplary display, the data is shown on four quadrants of the monitor. Quadrants 131 and 132 respectively display the images of the vehicle which were formed by cameras 42 and 44 at the first and second monitor stations (22 and 32 in FIG. 1). These images identify the make and color of the vehicle and preferably include the license plate. Because these quadrant displays are side by side, a system operator can quickly verify that the same vehicle was the source of the first and second emission concentrations that exceeded the standards.

The display on monitor quadrants 131 and 132 also preferably includes the date and time, a number assigned to the vehicle, emission concentrations (e.g., HC, NO, CO and $CO_2$) and data pertaining to concentration ratios (e.g., the slope of the ratio of $CO/CO_2$).

The display on monitor quadrant 133 preferably includes a comparison of the image of the license plate formed by the cameras 42 and 44 with the digitized license plate characters from the license plate reader (46 in FIG. 2). This display further verifies the visual identification of the vehicle. In addition, the digitized license plate characters are in a convenient form for storage along with the emission concentration data.

The display on monitor quadrant 134 preferably includes data related to the infrared sources (e.g., peak-to-peak output in absence of vehicles and exhaust plumes) and system calibration data. It also includes plots of the emission concentrations over a predetermined time interval (e.g., ~2 seconds) and plots of concentration ratios (e.g., $CO/CO_2$).

Thus, a large amount of data is presented in a compact form on a single monitor. This feature and the data storage feature discussed above facilitate a reduction of the number of personnel, e.g., to a single operator, needed for operation of the monitoring system 20. They also reduce the possibility of errors in identification of violating vehicles.

In a "lock-onto-high emitters" feature of the invention, a yes decision at decision step 112 momentarily freezes the display on video quadrant 131 as indicated by process step 138. This display freeze acts as a visual signal to alert the system operator to the fact that a moving vehicle has exceeded emission standards at the first monitor station. The operator can then concentrate on this vehicle to see if it is determined to be in violation in accordance with process steps 116, 118, 120 and 124. The absence of such a display freeze indicates that the emissions of passing vehicles are not exceeding concentration standards at the first monitor station and, therefore, the operator can perform other duties. This feature effects an efficient use of the operator's time.

In an alternative data-gathering mode of operation which is indicated by broken path lines 136 in FIG. 3, the collected data is stored in storage even if both first and second emission concentrations do not exceed the emission-concentration standards (in this mode. This optional mode is useful for preparing databases, e.g., comparison of emission concentrations of different vehicle types or manufacturers, to regulatory agencies.

Figure 5:
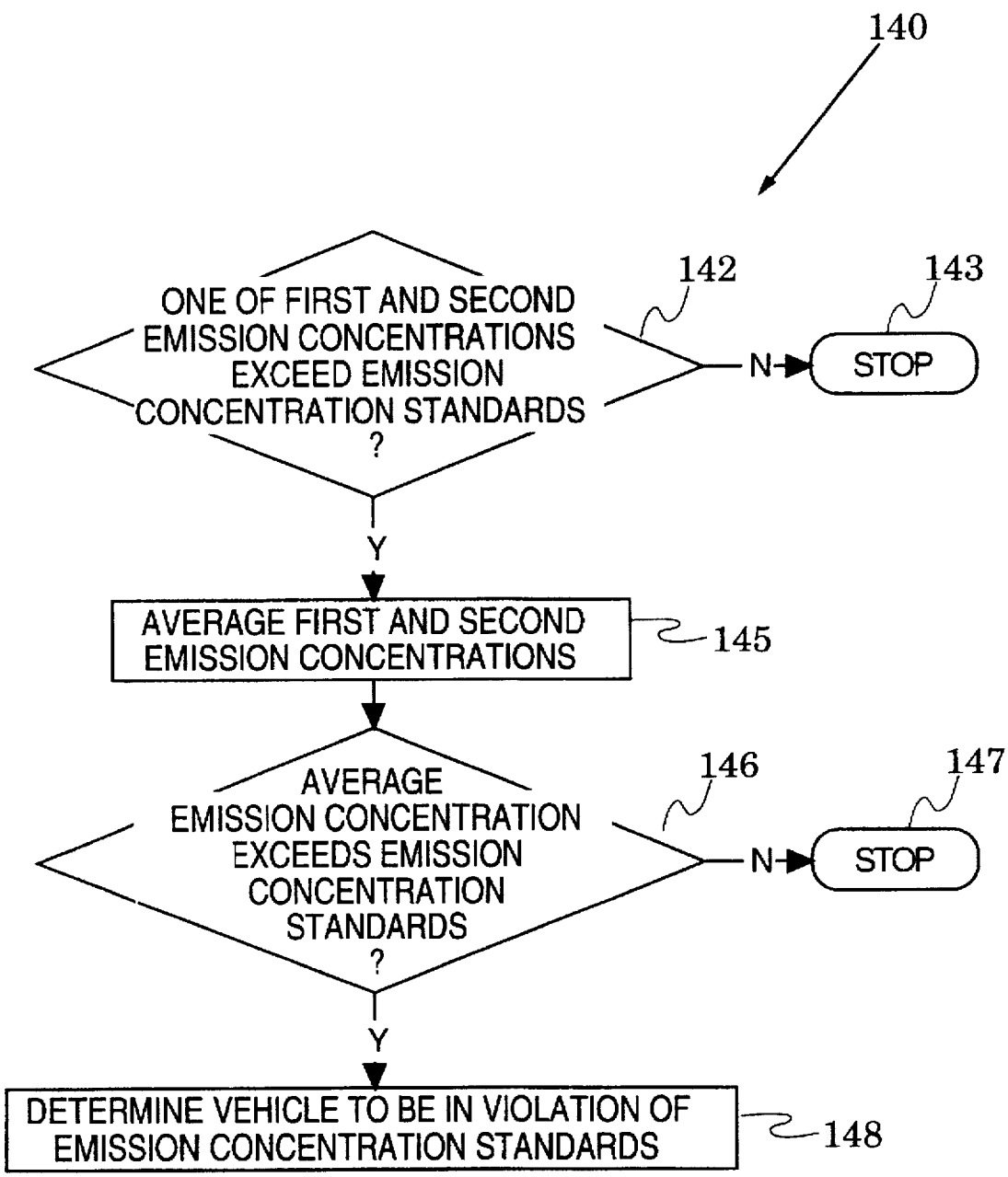
FIG. 5 is a flow diagram which illustrates another compliance operational mode of the monitoring system of FIG. 1.

Flow chart 140 of FIG. 5 illustrates an alternative compliance-mode embodiment. At decision step 142, this process stops at terminator 143 if both of the first and second emission concentrations do not exceed the emission-concentration standards and proceeds to process step 145 if at least one of them exceeds the standards. Process step 145 obtains an average of the first and second emission concentrations.

In decision step 146, the process stops at terminator 147 if the average does not exceed the emission-concentration standards and proceeds to the process step 124 (of FIG. 4) in which the vehicle is determined to be in violation of the emission-concentration standards. Although this compliance-mode process involves additional process steps, it has also been found to significantly reduce disagreements with subsequent IM240 emission-concentration tests.

Figure 6:
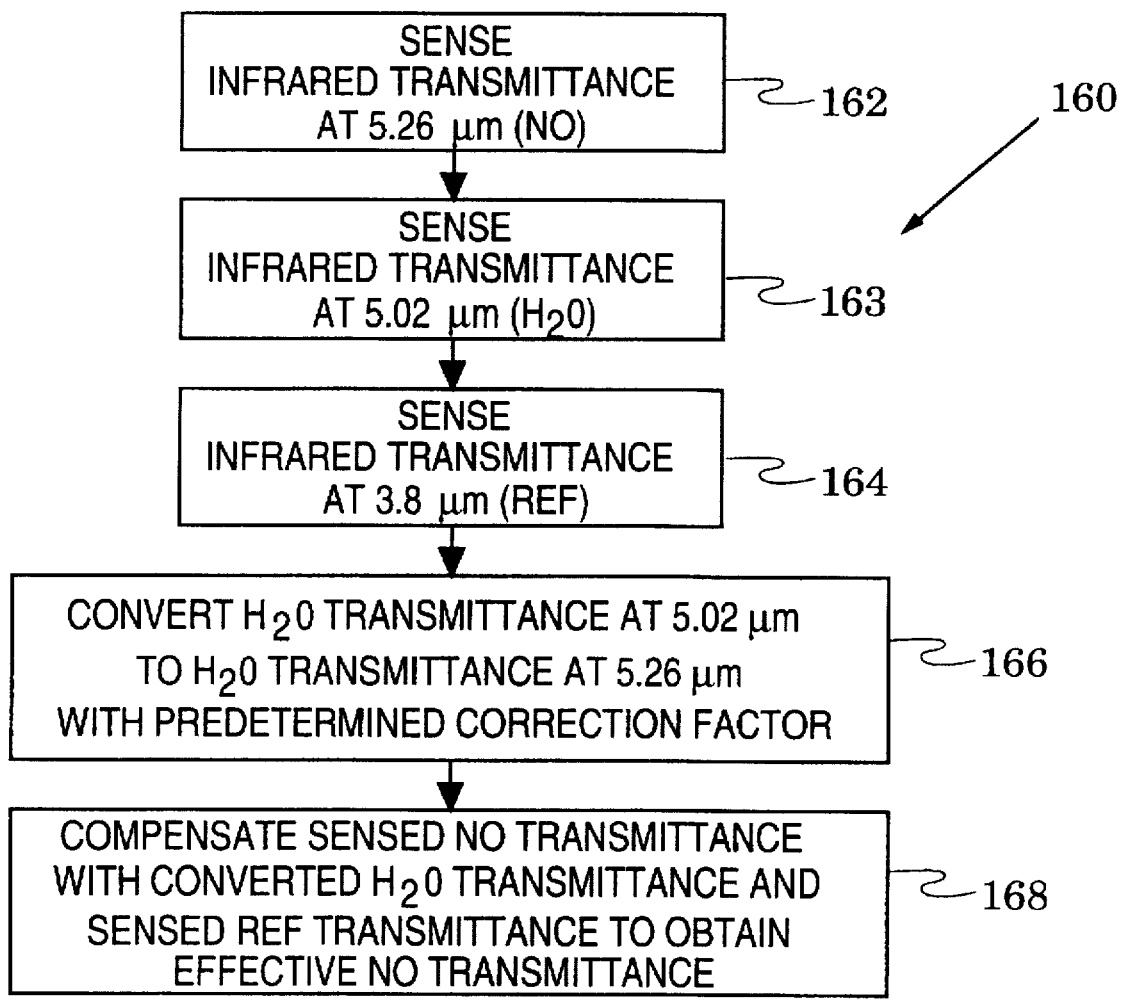
FIG. 6 is a flow diagram which shows an exemplary process for determining an effective NO transmittance when implementing the compliance mode of FIG. 4.
Figure 7:
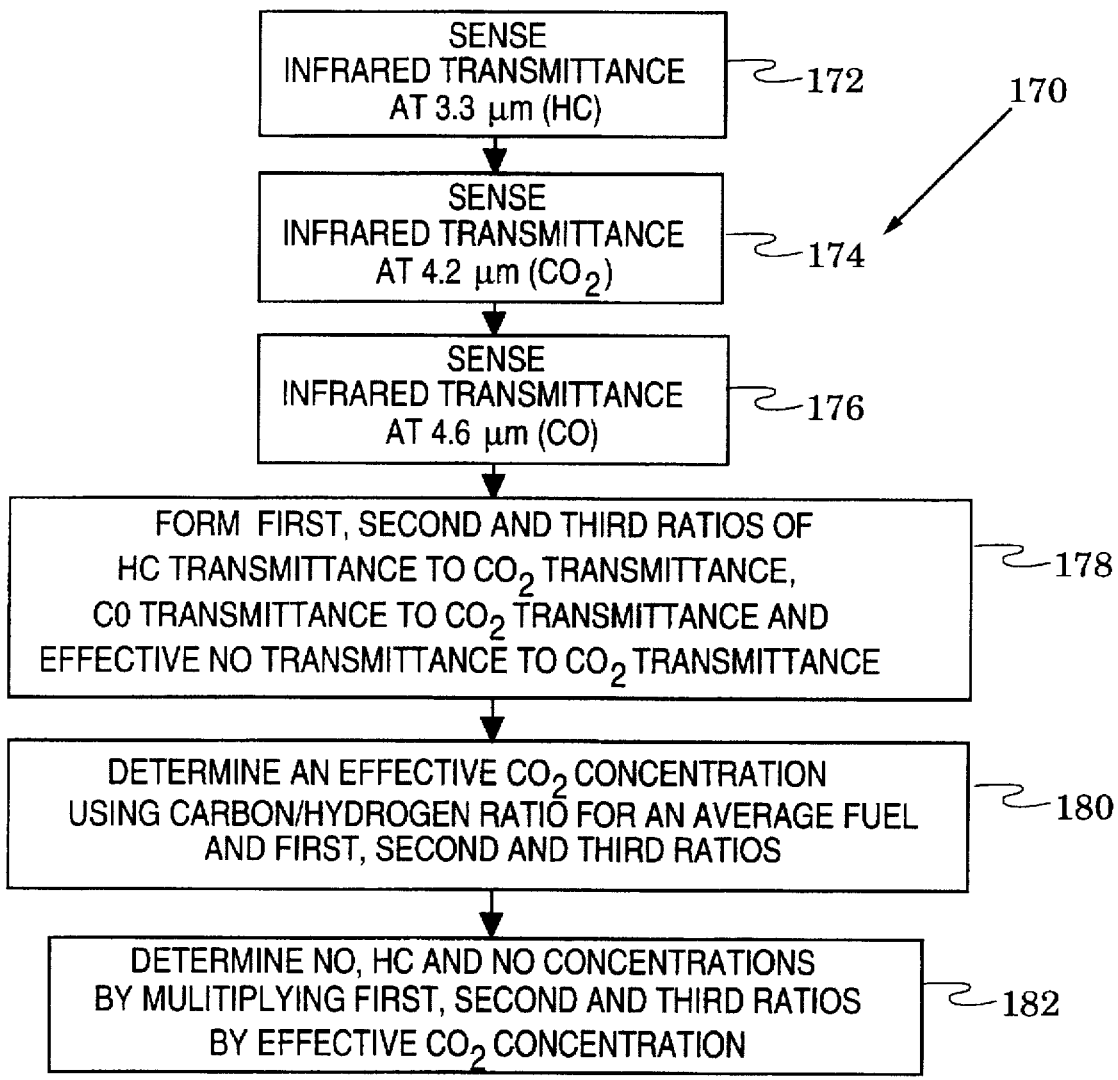
FIG. 7 is a flow diagram which shows an exemplary process for determining NO, HC, CO and $CO_2$ emission concentrations when implementing the compliance mode of FIG. 4.

Process steps 108 and 116 of the flow diagram 100 of FIG. 4 are directed to conversion of transmittances to emission concentrations. These steps can be performed with various processes known in the emission measurement art. For example, the data processor 50 can be programmed in accordance with the flow diagrams 160 and 170 of FIGS. 6 and 7.

The steps of flow diagram 160 compensate the sensed NO transmittance at the first and second monitor stations (22 and 32 in FIGS. 1 and 2) to find an effective NO transmittance. In process steps 162, 163 and 164, infrared transmittances are sensed at selected absorbing wavelengths (e.g., 5.26 μm for NO, 5.02 μm for $H_2O$ and 3.8 μm for a nonabsorbing reference). In process step 166, the $H_2O$ transmittance is converted to an $H_2O$ transmittance at 5.26 with a predetermined correction factor (stored, for example, in a lookup table). Finally, the sensed NO transmittance is compensated in process step 168 with the converted $H_2O$ transmittance and the sensed reference transmittance to obtain an effective NO transmittance which can be used with other sensed transmittances to obtain emission concentrations, e.g., as described below with reference to flow diagram 170 of FIG. 7.

Once an effective NO transmittance has been obtained, the emission concentrations are found with the operational steps of flow diagram 170. In process steps 172, 174 and 176, infrared transmittances are sensed at selected absorbing wavelengths (e.g., 3.3 μm for HC, 4.2 μm for $CO_2$ and 4.6 μm for CO). In process step 178, first, second and third ratios are formed of the NO transmittance (from the process of flow diagram 160 of FIG. 6) the HC transmittance and the CO transmittance to the $CO_2$ transmittance. An effective $CO_2$ concentration is then determined in process step 180 using these ratios and a predetermined carbon/hydrogen ratio for an average vehicle fuel. Finally, the HC, NO and CO concentrations are determined in process step 182 by multiplying the first, second and third ratios by the effective effective $CO_2$ concentration.

Monitoring systems of the invention reduce disagreement rates with fixed-facility tests (e.g., to <10%) when compared to single-station tests. This reduction enhances the attractiveness of such monitoring systems to law-enforcement and regulatory agencies.

Although a system embodiment of the invention has been described with reference to an infrared prototype, the teachings of the invention can be extended to other electromagnetic wavelengths which are absorbed by molecular species of interest, e.g., ultraviolet and microwave wavelengths, and also to the interrogation of other exhaust plumes, e.g., smokestack plumes and liquid and gas plumes of various manufacturing processes.

In an exemplary infrared prototype, the data processor 50 of FIGS. 1 and 2 was realized with dual computers that were dedicated to processing data respectively from monitor stations 22 and 32 to form emission concentrations and an off-line computer which was dedicated to the process of comparing the emission concentrations to concentration standards and making decisions.

While several illustrative embodiments of the invention have been shown and described, numerous variations and alternate embodiments will occur to those skilled in the art. Such variations and alternate embodiments are contemplated, and can be made without departing from the spirit and scope of the invention as defined in the appended claims.

We claim:

1. An emission-concentration monitoring system for determining compliance of moving vehicles to emission-concentration standards, comprising:

first exhaust-plume monitoring station which is positioned at a first location along a moving vehicle path and which has:
   a) a first source of electromagnetic radiation arranged to direct a first electromagnetic beam through an exhaust plume of a vehicle moving along said path; and
   b) a first set of electromagnetic detectors arranged to receive said first beam and configured to detect a plurality of first transmittances of said first beam at a plurality of selected wavelengths at which different molecular species absorb radiation of said first beam;

a second exhaust-plume monitoring station which is positioned at a second location along said path that is spaced from said first location by a sensing space and which has:
   a) a second source of electromagnetic radiation arranged to direct a second electromagnetic beam through an exhaust plume of a vehicle moving along said path; and
   b) a second set of electromagnetic detectors arranged to receive said second beam and configured to detect a plurality of second transmittances of said second beam at said selected wavelengths; and a data processor configured to:
   a) process said first and second transmittances respectively into a plurality of first and second emission concentrations;
   b) compare said first emission concentrations with a set of predetermined emission-concentration standards; and
   c) compare said second emission concentrations with said set of predetermined emission-concentration standards;

said first and second monitoring stations having a spatial separation which reduces compliance errors caused by temporal variability of vehicular emissions.

2. The system of claim 1, wherein said sensing space exceeds 3 meters.

3. The system of claim 1, wherein said sensing space exceeds 15 meters.

4. The system of claim 1, wherein said electromagnetic radiation is infrared radiation with wavelengths substantially spanning the 3–6 μm region.

5. The system of claim 1, further including:

a first imaging device positioned to form an image of said vehicle when it is substantially at said first location; and a second imaging device positioned to form an image of said vehicle when it is substantially at said second location.

6. The system of claim 5, wherein at least one of said first and second imaging devices is a camera.

7. The system of claim 5, wherein at least one of said first and second imaging devices includes:

a video camera; and a character reading and digitizing processor.

8. The system of claim 1, further including a display device which is coupled to said data processor for displaying at least one of said first and second emission concentrations.

9. The system of claim 1, wherein said data processor includes a storage device coupled to said data processor and said data processor is configured to store said first and second emission concentrations in said storage device if they both exceed said emission-concentration standards.

10. The system of claim 1, wherein said first and second sets of electromagnetic detectors each include:

a plurality of optical bandpass filters, wherein each of said optical filters is configured to pass a respective one of said selected wavelengths; and a plurality of photoconductive detectors each positioned to receive filtered electromagnetic radiation from a respective one of said filters.

11. The system of claim 1, wherein said molecular species include nitric oxide, hydrocarbons, carbon monoxide and carbon dioxide.

12. The system of claim 1, wherein said data processor is configured to form ratios of selected ones of said transmittances and multiply said ratios by a predetermined carbon dioxide concentration.

13. The system of claim 1, wherein said data processor is configured to generate an alert if said first and second emission concentrations both exceed said emission-concentration standards.

14. The system of claim 1, wherein said first and second radiation sources are each a glow bar which generates infrared radiation.

15. A method of determining compliance of moving vehicles to emission-concentration standards, comprising the steps of:

passing a first beam of electromagnetic radiation through an exhaust plume of a moving vehicle at a first location along a path of said vehicle;

passing a second beam of electromagnetic radiation through said exhaust plume at a second location along said path which is spaced from said first location by a sensing space;

sensing, at a plurality of selected wavelengths at which different molecular species absorb said electromagnetic radiation, a plurality of first transmittances of said first beam;

sensing, at said plurality of selected wavelengths, a plurality of second transmittances of said second beam;

converting said first and second transmittances respectively into a plurality of first and second emission concentrations;

comparing said first emission concentrations to said emission-concentration standards;

comparing said second emission concentrations to said emission-concentration standards; and determining said vehicle to be in violation of said emission concentration standards if both of said first and second emission concentrations exceed said emission concentration standards and not in violation of said emission concentration standards if at least one of said first and second emission concentrations does not exceed said emission concentration standards.

16. The method of claim 15, further including the step of selecting said sensing space to exceed 3 meters.

17. The method of claim 15, further including the step of selecting said sensing space to exceed 15 meters.

18. The method of claim 15, further including the step of configuring said first and second beams to include infrared wavelengths across a 3 to 6 micrometer region.

19. The method of claim 15, further including the step of selecting said selected wavelengths to include wavelengths absorbed by nitric oxide, hydrocarbons, carbon monoxide and carbon dioxide.

20. The method of claim 15, further including the steps of:
visually identifying said vehicle at said first location; and
visually identifying said vehicle at said second location.

21. The method of claim 20, wherein said identifying steps each include the step of forming an image of said vehicle.

22. The method of claim 21, further including the step of storing said first and second emission concentrations and said vehicle image.

23. The method of claim 15, wherein said identifying steps each include the step of forming an image of the license plate of said vehicle.

24. The method of claim 23, further including the step of storing said first and second emission concentrations and said license plate image.

25. The method of claim 15, further including the step of storing said first and second emission concentrations if said first and second emission concentrations both exceed said emission concentration standards.

26. The method of claim 15, further including the steps of:
alerting a law-enforcement agency if both of said first and second emission concentrations exceed said emission concentration standards; and
providing said law-enforcement agency with a visual identification of said vehicle.

27. The method of claim 15, wherein said converting step includes, for each of said first and second transmittances, the steps of:
forming ratios of selected ones of said transmittances; and
multiplying said ratios by a predetermined carbon dioxide concentration.

28. A method of determining compliance of moving vehicles to emission-concentration standards, comprising the steps of:

passing a first beam of electromagnetic radiation through an exhaust plume of a moving vehicle at a first location along a path of said vehicle;

passing a second beam of electromagnetic radiation through said exhaust plume at a second location along said path which is spaced from said first location by a sensing space that exceeds 1 meter;

sensing, at a plurality of selected wavelengths at which different molecular species absorb said electromagnetic radiation, a plurality of first transmittances of said first beam;

sensing, at said plurality of selected wavelengths, a plurality of second transmittances of said second beam;

converting said first and second transmittances respectively into a plurality of first and second emission concentrations;

comparing said first emission concentrations to said emission-concentration standards;

comparing said second emission concentrations to said emission-concentration standards; and determining said vehicle to be in violation of said emission concentration standards if an average of said first second emission concentrations exceeds said emission concentration standards and not in violation of said emission concentration standards if said average does not exceed said emission concentration standards.

29. The method of claim 28, further including the step of selecting said sensing space to exceed 3 meters.

30. The method of claim 28, further including the step of selecting said sensing space to exceed 15 meters.

31. The method of claim 28, further including the step of selecting said selected wavelengths to include wavelengths absorbed by nitric oxide, hydrocarbons, carbon monoxide and carbon dioxide.

32. The method of claim 28, further including the steps of:
visually identifying said vehicle at said first location; and
visually identifying said vehicle at said second location.

* * * * *